(12) United States Patent
Matsumoto

(10) Patent No.: US 7,469,799 B2
(45) Date of Patent: Dec. 30, 2008

(54) MEASUREMENT INSTRUMENT

(75) Inventor: Daisuke Matsumoto, Kyoto (JP)

(73) Assignee: Arkray, Inc., Kyoto (JP)

( * ) Notice: Subject to any disclaimer, the term of this patent is extended or adjusted under 35 U.S.C. 154(b) by 886 days.

(21) Appl. No.: 10/505,853

(22) PCT Filed: Feb. 28, 2003

(86) PCT No.: PCT/JP03/02305

§ 371 (c)(1),
(2), (4) Date: Aug. 26, 2004

(87) PCT Pub. No.: WO03/073091

PCT Pub. Date: Sep. 4, 2003

(65) Prior Publication Data

US 2005/0095173 A1  May 5, 2005

(30) Foreign Application Priority Data

Feb. 28, 2002 (JP) .............................. 2002-054895

(51) Int. Cl.
*B65H 59/02* (2006.01)
(52) U.S. Cl. .................. 221/270; 221/272; 221/268; 221/276; 221/287; 422/68.1; 422/102
(58) Field of Classification Search .............. 221/197, 221/224, 245, 255, 262, 268, 270, 272, 287; 422/58, 61, 99, 102, 104, 165
See application file for complete search history.

(56) References Cited

U.S. PATENT DOCUMENTS

| | | | |
|---|---|---|---|
| 5,395,504 A | 3/1995 | Saurer et al. | |
| 5,854,074 A | 12/1998 | Charlton et al. | |
| 7,327,451 B2 * | 2/2008 | Markart | ..................... 356/244 |
| 2003/0191415 A1 * | 10/2003 | Moerman et al. | ........... 600/584 |

FOREIGN PATENT DOCUMENTS

| | | |
|---|---|---|
| EP | 0 373 629 | 6/1990 |
| EP | 0 645 627 | 3/1995 |
| EP | 0 732 590 | 9/1996 |
| JP | 6-294769 | 10/1994 |
| JP | 8-262026 | 10/1996 |
| JP | 9-184819 | 7/1997 |
| JP | 9-250998 | 9/1997 |
| JP | 10-253570 | 9/1998 |
| JP | 2001-141686 | 5/2001 |
| JP | 2001-281199 | 10/2001 |
| JP | 2003-42994 | 2/2003 |
| WO | WO 01/63272 | 8/2001 |

* cited by examiner

*Primary Examiner*—Jill Warden
*Assistant Examiner*—Cedric A Chan
(74) *Attorney, Agent, or Firm*—Hamre, Schumann, Mueller & Larson, P.C.

(57) ABSTRACT

A measuring instrument (A) includes a pressurizing mechanism (C) which moves at least one of a measuring article (S) and a connector (4) toward and into pressing contact with the other when the measuring article (S) is placed at a measuring position (P). This prevents improper connection between the connector (4) and the measuring article (S) caused by wear of the connector (4).

10 Claims, 11 Drawing Sheets

MEASUREMENT INSTRUMENT

TECHNICAL FIELD

The present invention relates to measuring instruments and related techniques used in such an application as measuring the glucose level in human blood.

BACKGROUND ART

As a conventional example in the field of measuring instrument, a device is known in which a cartridge loaded with a plurality of sensors is set to a predetermined position, and an operation is made to a sensor dispensing mechanism for taking a sensor, one at a time, out of the cartridge to a predetermined measuring position (See JP-A 8-262026 for example). The sensor is, for example, a small piece containing a reagent which reacts with e.g. glucose in the blood, and provided with a pair of electrodes. Near the measuring position, a connector is provided, which makes contact with the pair of electrodes of the sensor when the sensor comes to the measuring position. With such an arrangement, when the reagent in the sensor makes contact with the blood of the user, a measurement circuit in the measuring instrument measures a glucose level in the blood, and a result of the measurement is displayed in a display. Such a measuring instrument enables easy measurement of blood glucose level.

However, according to the conventional art, when the sensor is transported to the measuring position, the sensor is rubbed strongly against the connector in order to make sure that the sensor has a reliable contact with the connector. Thus, in the conventional art, the electrodes of the connector and the sensor wear out after repeated use of the measuring instrument, which can lead to poor contact between the components. Further, as the electrodes wear out, resulting powdery particles can stick to the connector and causes such problems as short circuit and reduced accuracy in the measurement.

DISCLOSURE OF THE INVENTION

An object of the present invention is to provide a measuring instrument capable of solving or reducing the above problem.

A measuring instrument provided by the present invention comprises measuring article transporting means for transportation of a measuring article from a predetermined set position to a measuring position for contact with a connector, and a measurement circuit for performing a measuring operation using the measuring article upon connection of the measuring article with the connector. The measuring instrument further comprises pressurizing means for moving at least one of the measuring article and the connector toward and into pressing contact with the other when the measuring article is at the measuring position.

Preferably, the pressurizing means includes a mechanism for moving the connector to the measuring article in a reciprocating manner.

Preferably, the connector moves away from the measuring position for avoiding contact with the measuring article during the transportation of the measuring article to the measuring position.

Preferably, the pressurizing means includes a supporting member supporting the connector and a pressing member separate from the supporting member. The pressing member makes a first operation of pressing a first surface of the supporting member to deform the supporting member for a movement of the connector away from the measuring article, and a second operation of pressing a second surface of the supporting member which is a surface away from the first surface to deform the supporting member for a movement of the connector toward the measuring article.

Preferably, the supporting member extends in a predetermined direction and includes a first and a second cutout recesses spaced from each other longitudinally of the supporting member. The pressing member makes a forward movement from a predetermined initial position on a side of the first surface of the supporting member, passes through the first cutout recess after the first operation and moves on a side of the second surface of the supporting member. The pressing member then makes a rearward movement in a reverse direction of the forward movement after the second operation, passes through the second cutout recess and comes back to the initial position.

Preferably, the supporting member includes a ramp between the first and the second cutout recesses. The pressing member presses the ramp during the forward movement and the rearward movement for making the first and the second operations.

Preferably, the measuring article transporting means includes a movable member reciprocatable longitudinally of the supporting member. The pressing member is supported by the movable member for reciprocation with the movable member.

Preferably, the measuring instrument according to the present invention further comprises a stopper contactable with a rear end of the measuring article for preventing retraction of the measuring article once the measuring article is placed at the measuring position.

Preferably, the stopper extends out of the connector. The connector moves away from the measuring position during the transportation of the measuring article to the measuring position for preventing interference between the stopper and the measuring article, whereas the connector moves closer to the measuring article after the transportation of the measuring article for placing the stopper behind the measuring article.

Preferably, the measuring instrument according to the present invention further comprising a casing formed with an opening for exposure of at least part of the measuring article placed at the measuring position, and the measuring article transporting means is capable of discharging the measuring article from the opening out of the casing.

Preferably, the connector moves away from the measuring position when the measuring article is discharged from the opening out of the casing.

Preferably, the measuring article transporting means includes a movable member for pushing to move the measuring article. The movable member moves to discharge the measuring article out of the casing while making contact with the connector, thereby pushing the connector away from the measuring position.

Other characteristics and advantages of the present invention will become clearer from the description of the mode of embodiment to be given hereafter.

BEST MODE FOR CARRYING OUT THE INVENTION

Hereinafter, preferred embodiments of the present invention will be described specifically, with reference to the drawings.

Figure 1:
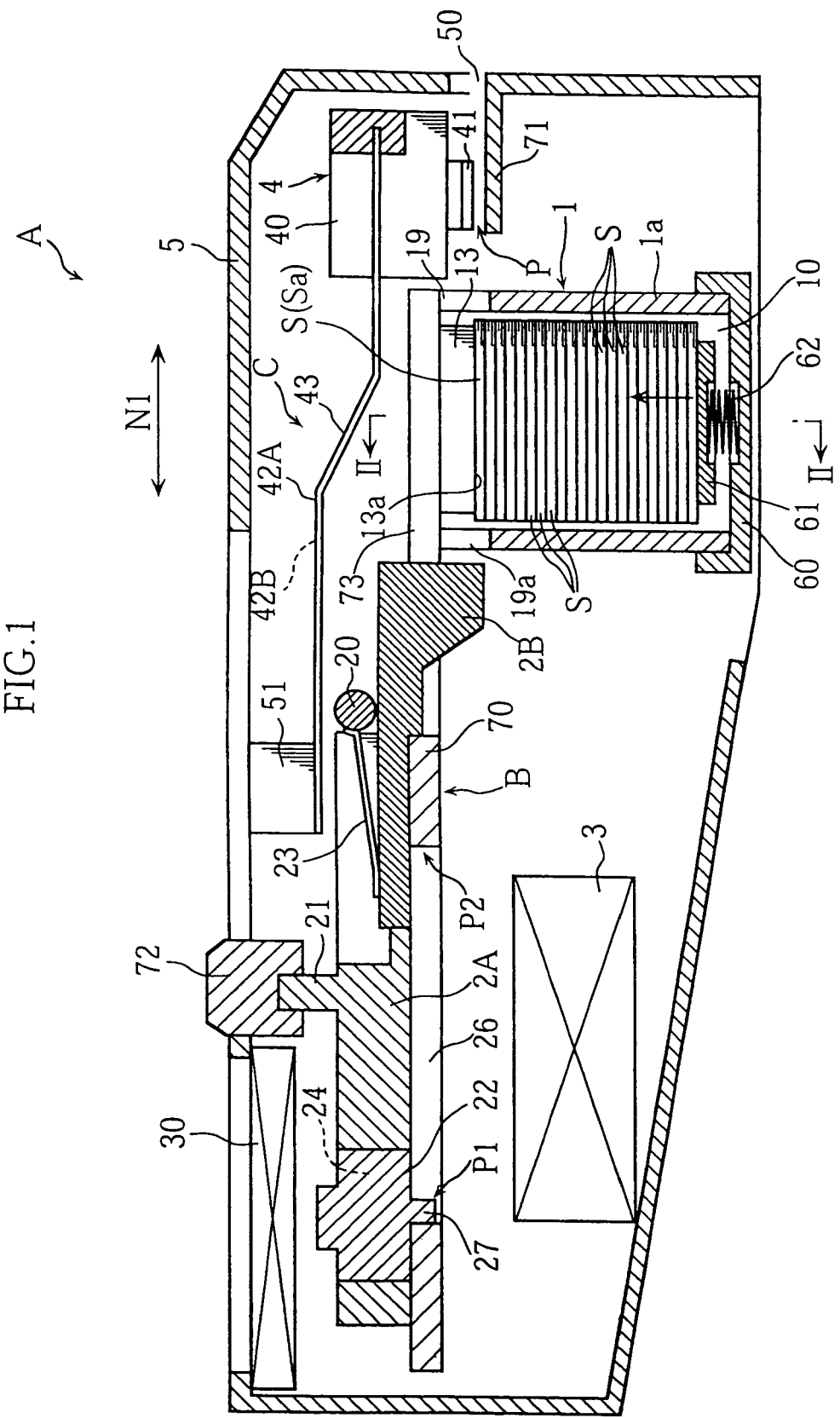
FIG. 1 is a simplified sectional view of a measuring instrument as an embodiment of the present invention.
Figure 2:
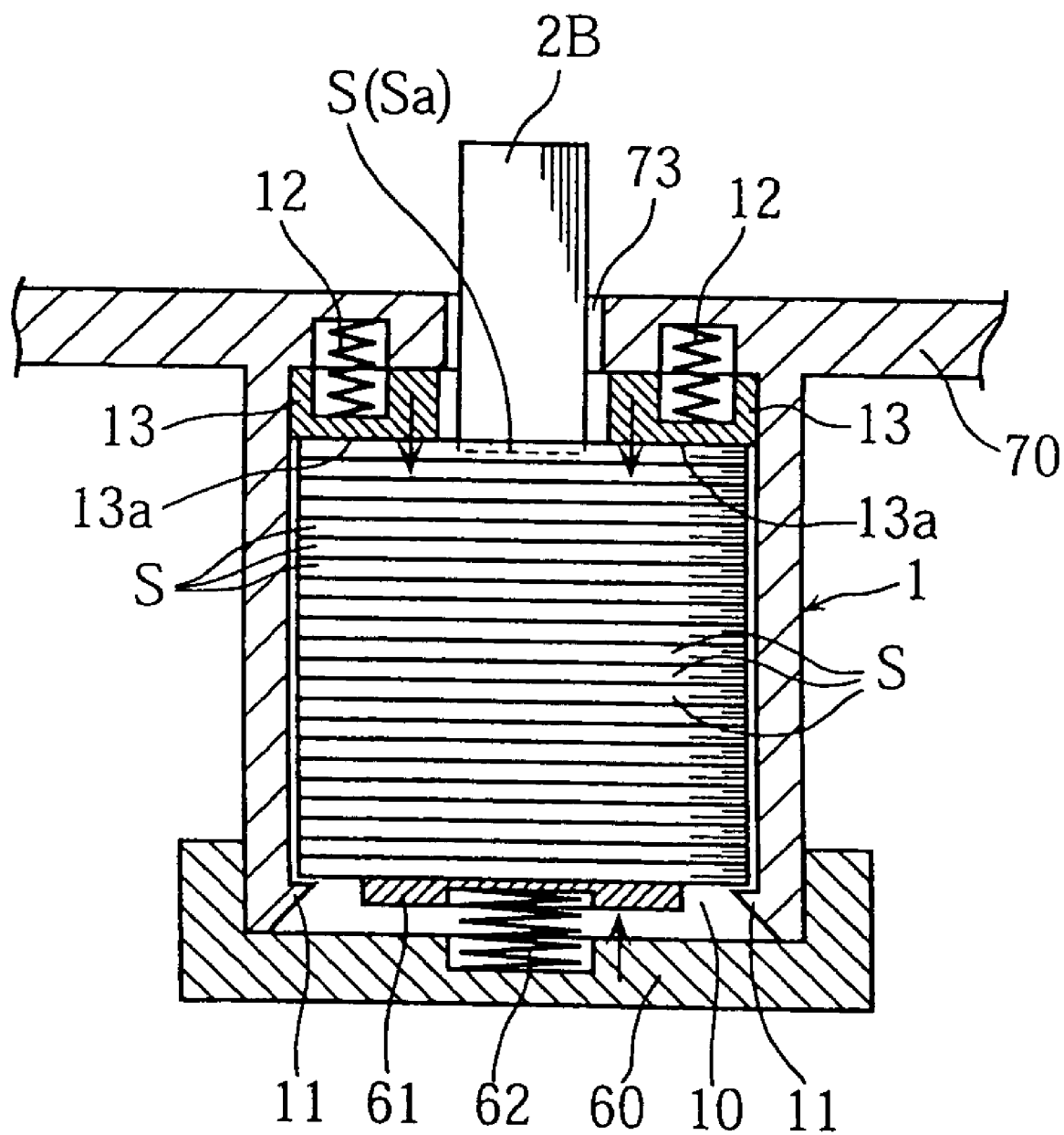
FIG. 2 is a sectional view taken in lines II-II in FIG. 1.

FIG. 1 and FIG. 2 show a measuring instrument according to the present invention. As clearly shown in FIG. 1, a measuring instrument A according to the present invention includes: a storage 1 for storing a plurality of sensors S; a sensor dispensing mechanism B for taking a sensor S out of the storage 1 to a predetermined measuring position P; a measurement circuit 3; a connector 4; a connector pressurizing mechanism C and a casing 5 which houses all of these. The sensor S is a small piece containing a reagent which reacts with glucose and a pair of electrodes (none of these are illustrated) contacted with the reagent.

The storage 1 is like a box, capable of storing a stack of sensors S, and has a wall 1a in the form of a rectangular tube. The wall 1a has an upper end connected to a lower surface of a base member 70 fixed in the casing 5. The wall 1a has an upper portion formed with a discharge port 19 for discharging a sensor S from the storage 1 in a forward direction (toward the right as in the drawing) and a cutout recess 19a facing the port. The cutout recess 19a provides a passage for a second movable member 2B to be described later. The storage 1 has a lower portion formed with an insertion port 10 which can be closed by a lid 60. When the lid 60 is detached, an appropriate quantity of the sensors S can be replenished from the insertion port 10. The lid 60 has a contact plate 61 which makes contact with the lowermost sensor S of the stack of sensors S loaded in the storage 1, and a spring 62 for urging the contact plate 61 in an upward direction. These members work to provide a constant upward urge to the sensors S in the storage 1.

As clearly shown in FIG. 2, a pair of contact plates 13 is provided inside the storage 1, not interfering with a path of the second movable member 2B. The uppermost sensor S (Sa) in the storage 1 makes contact with downward facing surfaces 13a of these contact plates 13, and is controlled to be at a predetermined height. The contact plates 13 are under an downward urge from a spring 12. This elastic urge is smaller than the elastic urge from the spring 62. Each contact plate 13 is pressed upward by the elastic urge of the spring 62, to make contact with the lower surface of the base member 70. The storage 1 has a lower inner wall provided with an opposed pair of stoppers 11. Each stopper 11 is elastically deformable to allow insertion of sensors S from below the insertion port 10 into the storage 10, and is engagable with the lowermost sensor S of the sensors S inserted in the storage 1 to prevent the sensors S in the storage 1 from dropping out of the insertion port 10. When the lid 60 is removed to replenish the storage 1 with sensors S, these stoppers 11 reliably eliminate possibilities that the sensor S in the storage may drop, making easy to replenish the sensors S.

Referring to FIG. 1, below the connector 4 is a support 71, a region on which is the measuring position P. The support 71 has a generally horizontal upper surface for supporting a sensor S which comes from the storage 1, and is ahead of the discharge port 19. The casing 5 is formed with an exposure/discharging opening 50 at a place ahead of the measuring position P.

The connector 4 includes a block 40 made of resin for example, which has a lower surface formed with metal terminals 41 for making contact with the pair of electrodes of the sensor S. The measurement circuit 3 includes a CPU, a memory and other relevant components, and is electrically connected to the connector 4. With the connector 4 electrically connected to the electrodes of a sensor S placed at the measuring position P, and the sensor S having its reagent wetted by a human blood, the measurement circuit 3 is capable of obtaining a glucose level in the blood, based on variation etc. of an electric current passed through the reagent after the blood is introduced. Values of the glucose level and other information obtained by the measurement circuit 3 are displayable on a display 30 provided by a liquid crystal panel for example.

Figure 3:
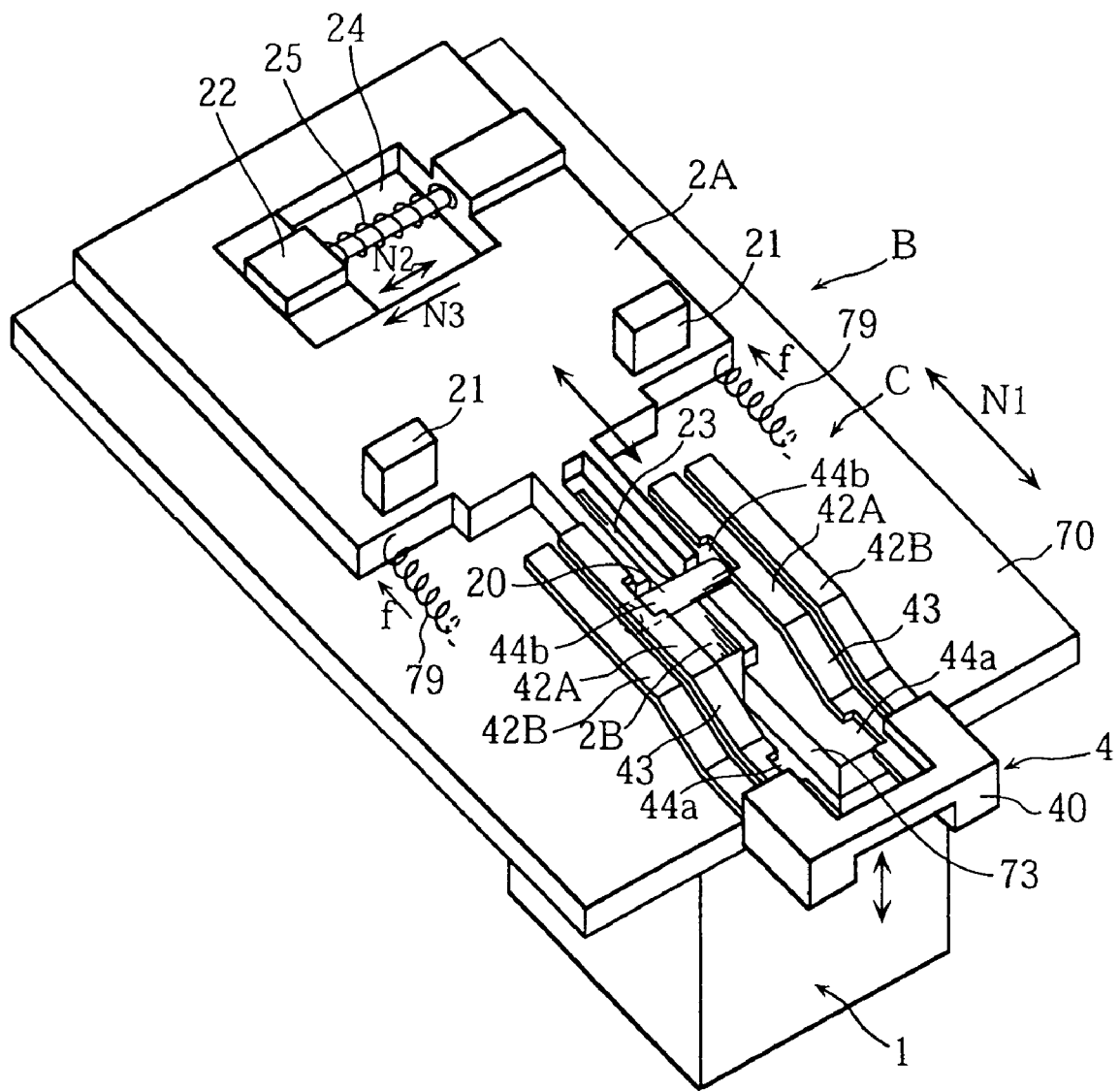
FIG. 3 is a simplified perspective view of a sensor dispensing mechanism used in the measuring instrument in FIG. 1.

The connector pressurizing mechanism C includes, as shown in FIG. 3, a pair of first supporting members 42A and a pair of second supporting members 42B supporting the connector 4, and a pusher 20.

Each of these first and the second supporting members 42A, 42B is provided by a metal leaf spring extending in longitudinal directions N1 of the measuring instrument A, and has a cantilever structure, i.e. having its one end attached to an upper wall of the casing 5 via a bracket 51, while the other end connected to the connector 4 (See FIG. 1). Although not illustrated in the drawings, each of the second supporting members 42B is electrically connected to the terminals 41 of the connector 4, serving as part of wiring which establishes electrical connection of the terminals 41 with the measurement circuit 3. The terminals 41 can be formed integrally with the second supporting members 42B. The connector 4 may not be supported by the second supporting members 42B but supported by only the first supporting members 42A. Therefore, according to the present invention, electrical connection between the connector 4 and the measurement circuit 3 may be achieved by electric wires instead of the second supporting members 42B. Each of the first supporting members 42A has a forwardly down-sloping ramp 43 in its longitudinally intermediate portion, and a first and a second cutouts 44a, 44b sandwiching the ramp 43 from front and rear. As will be described later, these portions work with a pusher 20, helping the connector 4 to do predetermined rising and lowering operations.

The pusher 20, which is columnar for example, pushes and elastically deforms each of the first supporting members 42A in vertical directions. The pusher 20, which is supported by the second movable member 2B of the sensor dispensing mechanism B via the leaf spring 23, can rise and lower as well as reciprocate in the longitudinal directions N1 together with the second movable member 2B. As will be described later, the reciprocation of the pusher 20 generates predetermined operations such as pushing the ramp 43 of the first supporting member 42A, and making a vertical passing through the first and the second cutout recesses 44a, 44b.

The sensor dispensing mechanism B includes a first and a second movable members 2A, 2B, and a movable block 22. The first movable member 2A has a pair of projections 21 for engagement with an operating tab 72 which is on the upper surface of the casing 5, and is capable of reciprocating in the longitudinal directions N1 of the measuring instrument A, on the base member 70 when operated via the operating tab 72. The second movable member 2B is ahead of the first movable member 2A, and is capable of reciprocating together with the first movable member 2A in the same directions. The first and the second movable members 2A, 2B are under constant rearward elastic urge f from e.g. a pair of springs 79 shown in FIG. 3. Thus, when moving these first and the second movable members 2A, 2B in the forward direction, the operating tab 72 must be pressed in the forward direction against the elastic urge f. It should be noted that according to the present embodiment, the first and the second movable members 2A, 2B are formed separately. However, according to the present invention, they may be formed integrally with each other. The base member 70 supports the storage 1, guides the first and the second movable members 2A, 2B in their sliding movement, and has a slit 73 which communicates with the discharge port 19 and the cutout recess 19a of the storage 1. The second movable member 2B is capable of passing through the slit 73, the cutout recess 19a and the discharge port 19 for pushing an uppermost sensor S (Sa) in the storage 1 toward the measuring position P.

Figure 4:
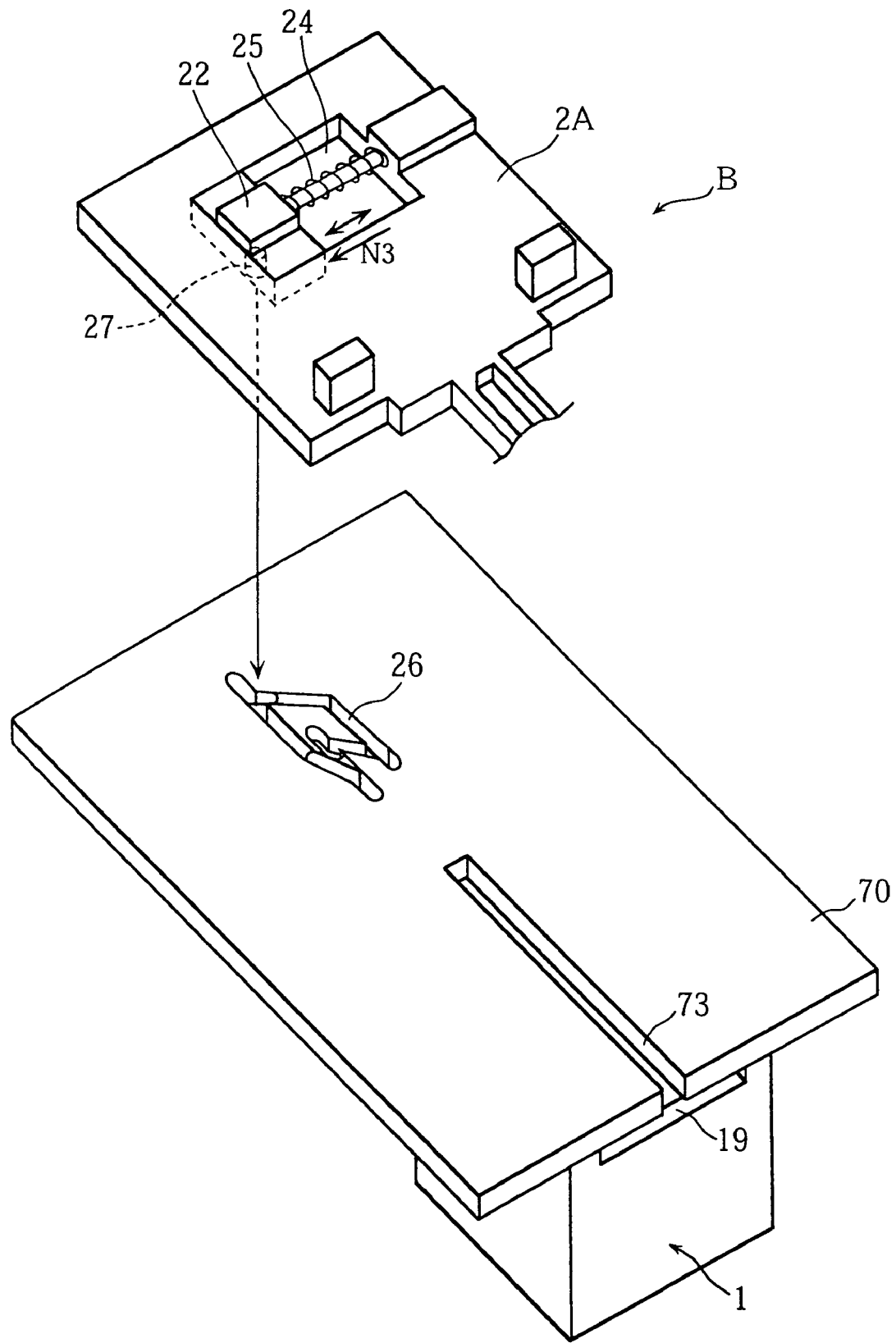
FIG. 4 is an exploded perspective view of a primary portion in the sensor dispensing mechanism used in the measuring instrument in FIG. 1.

The movable block 22 fits in an opening 24 formed in the first movable member 2A and is movable in widthwise directions N2 of the measuring instrument A. The movable block 22 is constantly urged by a spring 25 in a direction indicated by Arrow N. As shown clearly in FIG. 4, the base member 70 is provided with a cam groove 26 whereas the movable block 22 has a bottom surface formed with a downward facing pin 27 which fits in the cam groove 26.

Figure 5:
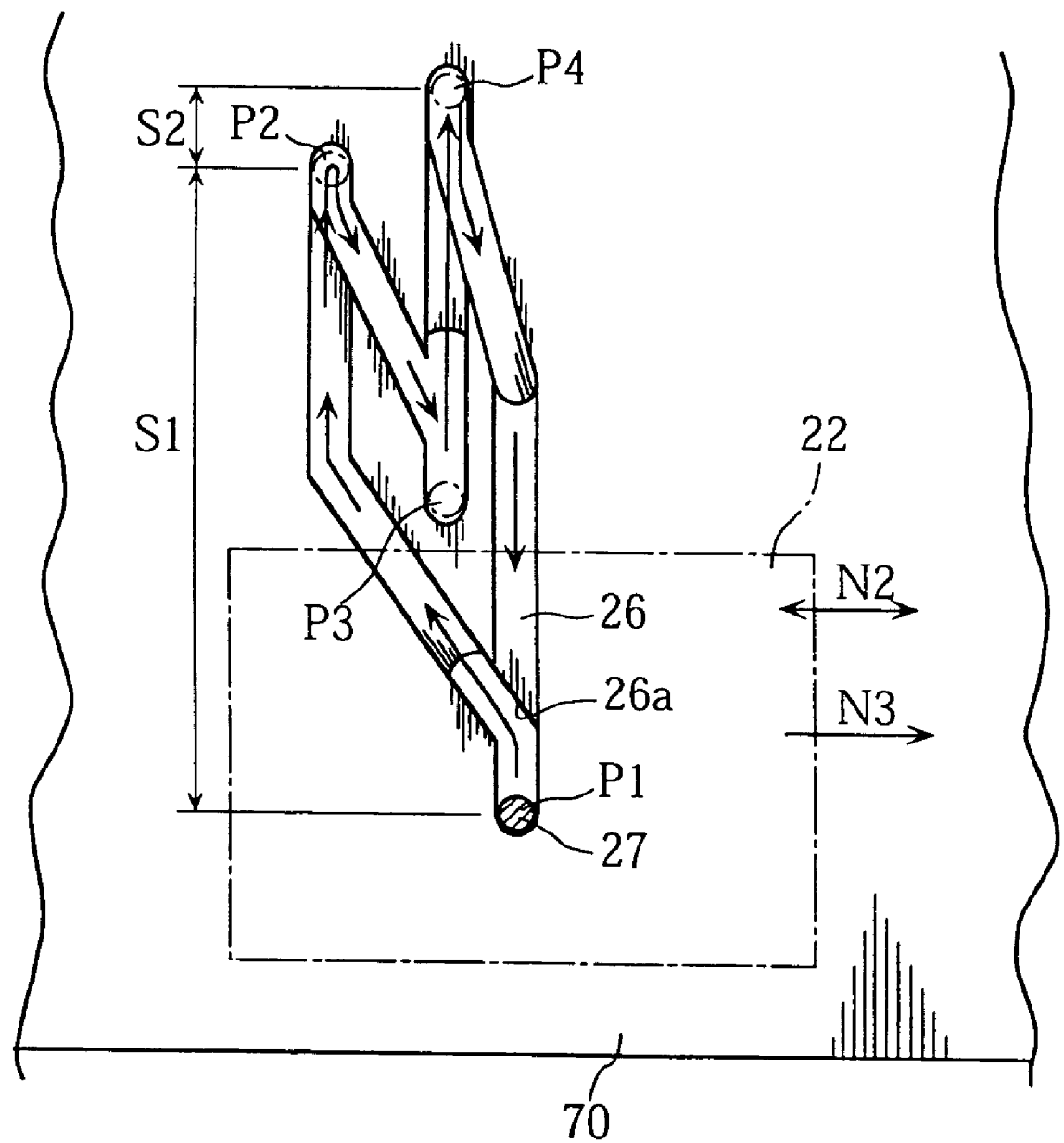
FIG. 5 is a plan view of a primary portion in FIG. 4.

The cam groove 26 is shaped as shown in FIG. 5. The upward direction in FIG. 5 is the forward direction of the measuring instrument A. When the first and the second movable members 2A, 2B are at their most rearward positions, the pin 27 is at a first position P1 in the cam groove 26. When the first and the second movable members 2A, 2B are reciprocated, the pin 27 moves forward for a predetermined distance S1 or to a second position P2 in the cam groove 26, and then moves back to a third position P3, and then forward to a fourth position P4, before coming back to the first position P1. With such an arrangement, a cycle of moving operations of the first and the second movable members 2A, 2B includes two forward movements. The fourth position P4 is ahead of the second position P2 by a predetermined dimension S2. This allows the first and the second movable members 2A, 2B to reach a farther point in their second forward movement than in the first forward movement of the first and the second movable members 2A, 2B. When the pin 27 moves in widthwise directions N2, the movable block 22 moves in the widthwise directions N2, while the first movable member 2A will not move together in the same directions. As has been described, the movable block 22 is constantly urged by the spring 25 in the direction N3. Thus, when the pin 27 moves from the second position P2 to the third position P3, and when moving back from the fourth position P4 to the first position P1, the pin 27 moves in the direction N3 under the urge, making sure that these operations happen reliably. The pin 27 is contacted and guided by a wall 26a formed in the cam groove 26 when moving forward from the first position P1, so that it will not move toward the fourth position P4.

Next, description will cover an operation and function of the measuring instrument A.

Figure 6:
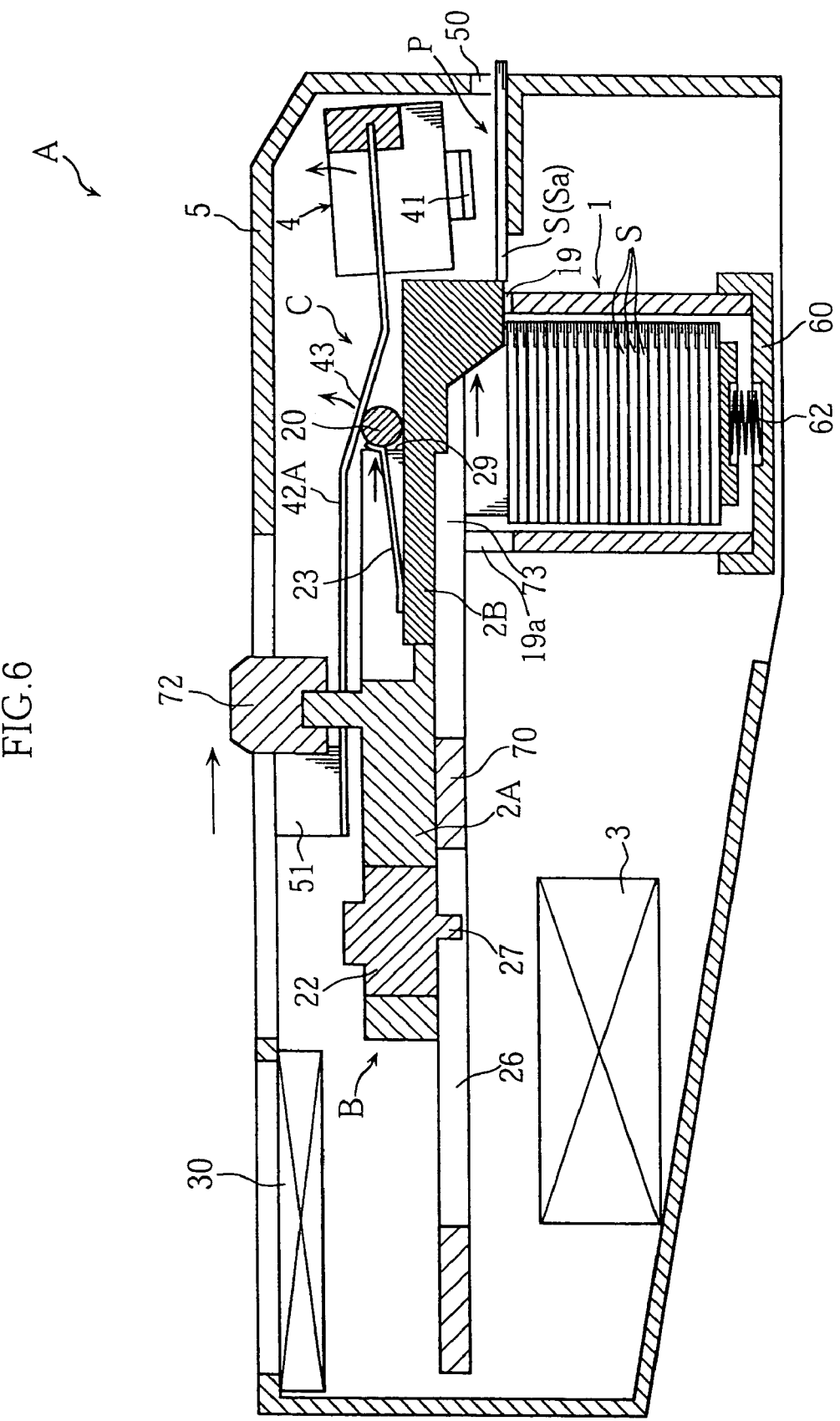
FIG. 6 is a simplified sectional view showing an operation of the measuring instrument in FIG. 1.

Starting from the situation in FIG. 1, the operating tab 72 is operated in the forward direction. This causes, as shown in FIG. 6, the first and the second movable members 2A, 2B to move forward, with the second movable member 2B having its tip pass through the slit 73. In this operation, the second movable member 2B pushes an uppermost sensor S (Sa) in the storage 1 ahead of the storage 1 to the measuring position P. As the second movable member 2B moves forward, the pusher 20 presses a lower surface of the ramp 43 of each first supporting members 42A. With the pusher 20 placed on the upper surface of the second movable member 2B, and with the pusher 20 having its rear making contact with an appropriate wall 29 of the first movable member 2A, it is possible to push the ramp 43 appropriately in the forward direction without causing the pusher 20 to lower or retract. When the pusher 20 presses the lower surface of the ramp 43, each first supporting member 42A deforms upward to raise the connector 4. Therefore, when a sensor S (Sa) is delivered to the measuring position P, the sensor S (Sa) will not make contact with the terminals 41, which protects the terminals 41 from wear, making the terminals serviceable in multiple times of use while assuring smooth transportation of the sensor S (Sa) to the measuring position P.

Figure 7:
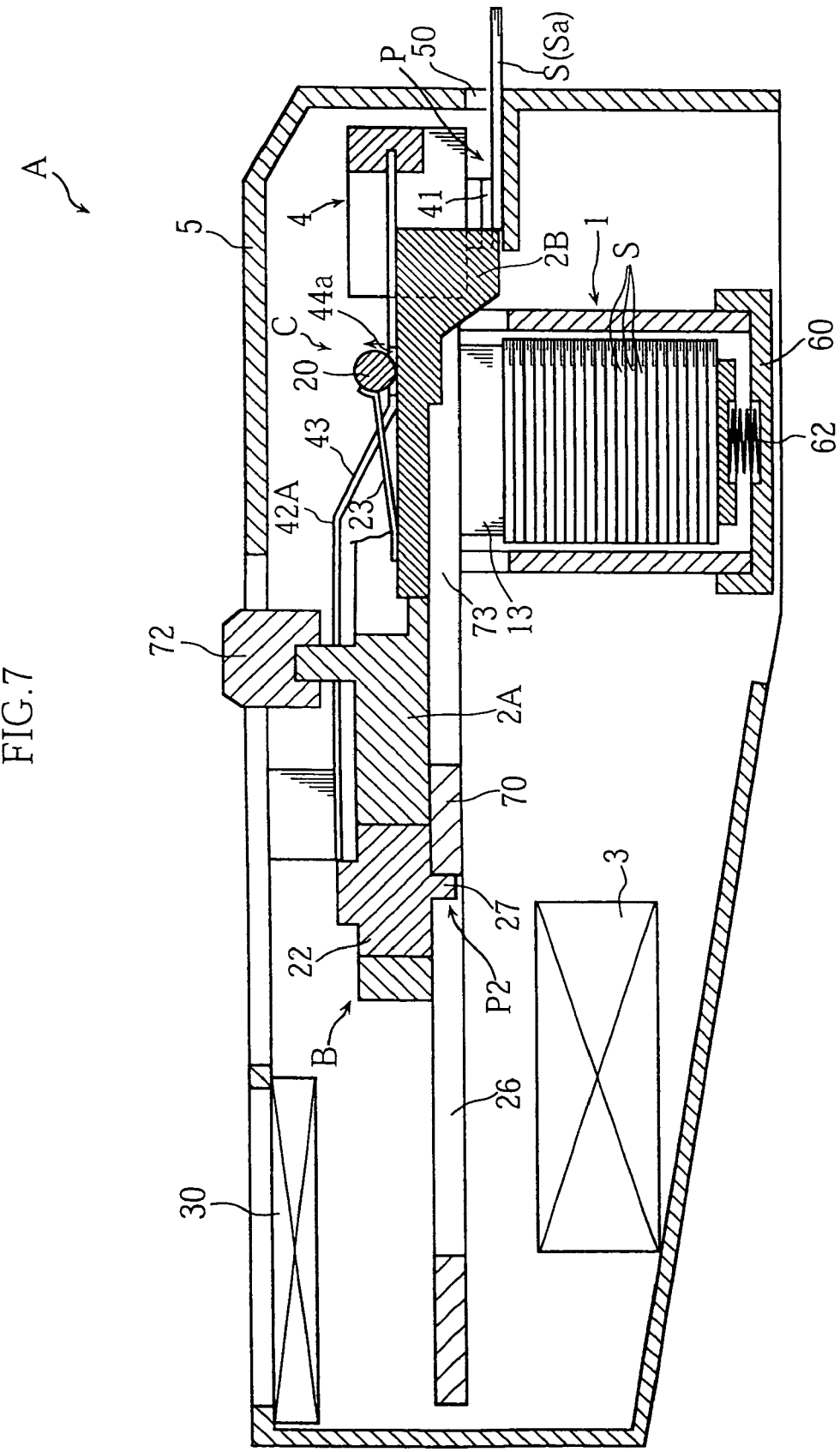
FIG. 7 is a simplified sectional view showing an operation of the measuring instrument in FIG. 1.

Next, as shown in FIG. 7, when the first and the second movable members 2A, 2B move further forward to bring the pin 27 to the second position P2 of the cam groove 26, the sensor S makes further forward movement, causing part of the sensor S projecting out of the casing 5, from the opening 50. On the other hand, the pusher 20 reaches where the first cutouts 44a are formed in the first supporting members 42A, passes through this place and thereby moves above each of the supporting members 42A. Thus, the pusher 20 no longer presses up the first supporting members 42A, which allows the connector 4 to come down to the initial height. In the above described forward movement of the first and the second movable members 2A, 2B is the first forward movement described with reference to FIG. 5. Successively, in order to make the second forward movement, the members must be retracted first. This rearward movement can be accomplished easily by an elastic urge provided by a pair of springs 79.

Figure 8:
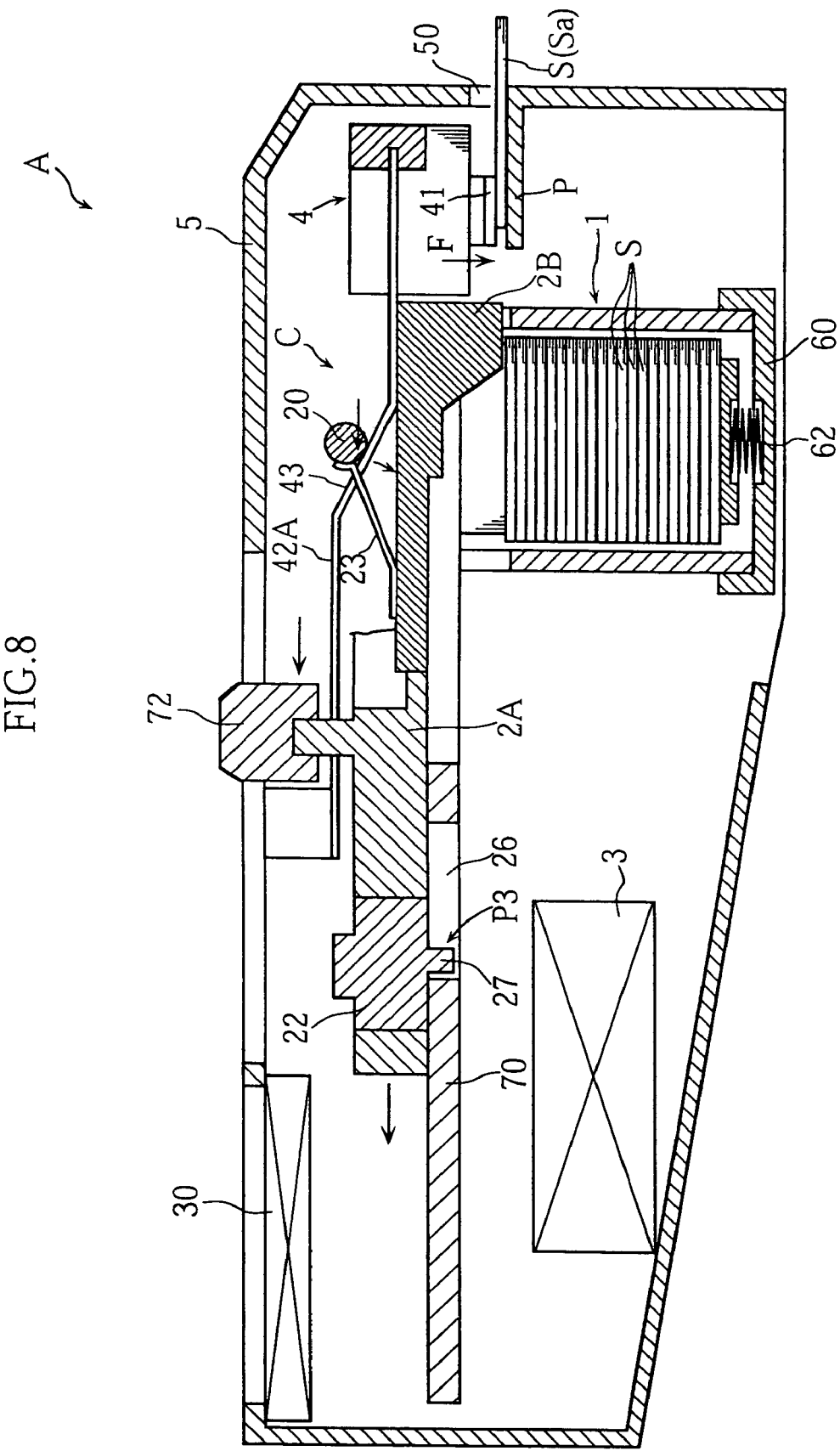
FIG. 8 is a simplified sectional view showing an operation of the measuring instrument in FIG. 1.

As shown in FIG. 8, the rearward movement of the first and the second movable members 2A, 2B brings the pin 27 to the third position P3 (A part of the cam groove 26 shown in FIG. 8 is not the same part as a part of the cam groove 26 shown in FIG. 1, FIG. 6 or FIG. 7. This also applies to FIG. 9 and FIG. 10). As understood, when the first and the second movable members 2A, 2B retract, the pusher 20 pushes rearward the upper surface of the ramp 43 of each supporting member 42A. The pushing force from the pusher 20 deforms each first supporting member 42A downward, exerting a downward force F on the connector 4. This makes the terminals 41 of the connector 4 be pressed onto the electrodes of the sensor S (Sa), establishing reliable electrical connections. While the connector 4 is being pressed onto the sensor S (Sa), the sensor S (Sa) is supplied with blood, and the measurement circuit 3 performs a measurement of glucose level in the blood.

Figure 9:
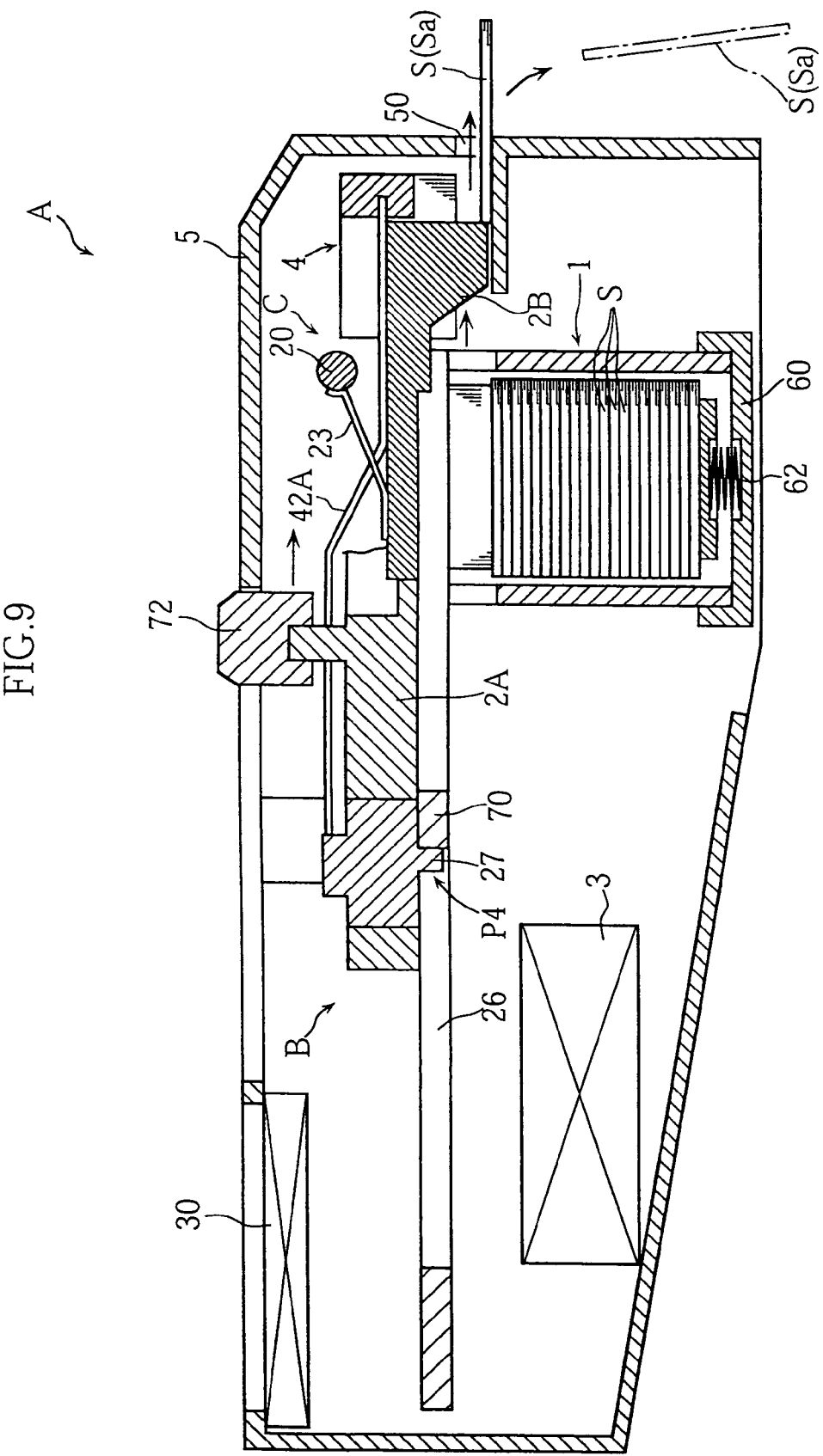
FIG. 9 is a simplified sectional view showing an operation of the measuring instrument in FIG. 1.
Figure 10:
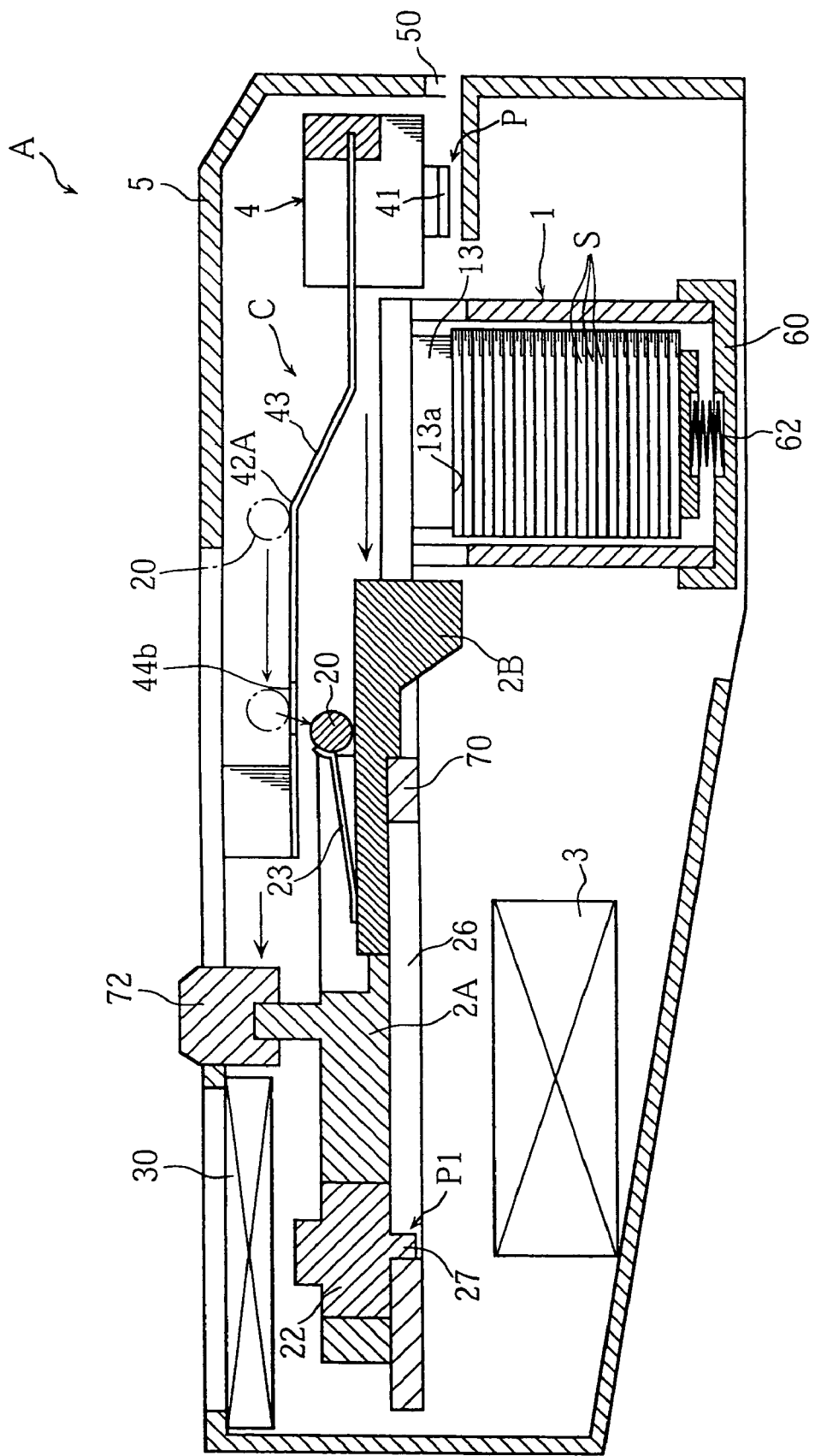
FIG. 10 is a simplified sectional view showing an operation of the measuring instrument in FIG. 1.

As shown in FIG. 9, the operating tab 72 is forwarded again thereafter, which makes the second forward movement of the first and the second movable members 2A, 2B, causing the second movable member 2B to push the sensor S (Sa) out of the casing 5 from the opening 50. Therefore, the user can dispose of the sensor S(Sa) without touching the sensor S (Sa), which is preferable in terms of sanitation. After finishing the second forward movement, as shown in FIG. 10, it becomes possible to move the first and the second movable members 2A, 2B back to the initial positions. Since the pusher 20 is displaceable in vertical directions, when the first and the second movable members 2A, 2B make the rearward movement, it is also possible to have the pusher 20 pass above the first supporting members 42A and through the second cutouts 44b as indicated by phantom lines in the drawing, thereby having the pusher 20 come back to its initial position. Though not illustrated in the drawings, the measuring instrument A includes a guide in order to smoothen the above described return travel of the pusher 20.

In the measuring instrument A according to the present invention, when the uppermost sensor S(Sa) of the sensors S stored in the storage 1 has been dispensed to the measuring position P, the next sensor S immediately below becomes a new uppermost sensor which then is dispensable to the measuring position P by the next cycle of operations of the first and the second movable members 2A, 2B. Therefore, it is possible to repeat the measuring process of the glucose level. Further, as mentioned earlier, the storage 1 can be replenished with an appropriate quantity of sensors S at any time. Therefore, when the user leaves home for a long period of time for example, he may conveniently carry the measuring instrument A with the storage 1 completely or sufficiently filled with the sensors S. The sensors S in the storage 1 are transported to the measuring position P in the same sequential order as the sensors S are loaded into the storage 1. This advantageously reduces an undesirable possibility that older sensors remain unused and deteriorates over time in the storage.

As described, the connector pressurizing mechanism C makes the pusher 20 move in a cycle of predetermined path, and press the first supporting member 42A in this movement, thereby bringing the connector 4 closer to and away from the sensor S. Since the mechanism is a simple structure, it is suitable for keeping manufacturing cost of the measuring instrument A as low as possible. The pusher 20 is driven by a reciprocating movement of the first and the second movable members 2A, 2B, which is more preferable for simplification of the entire structure as well as for making operations easier.

Figure 11:
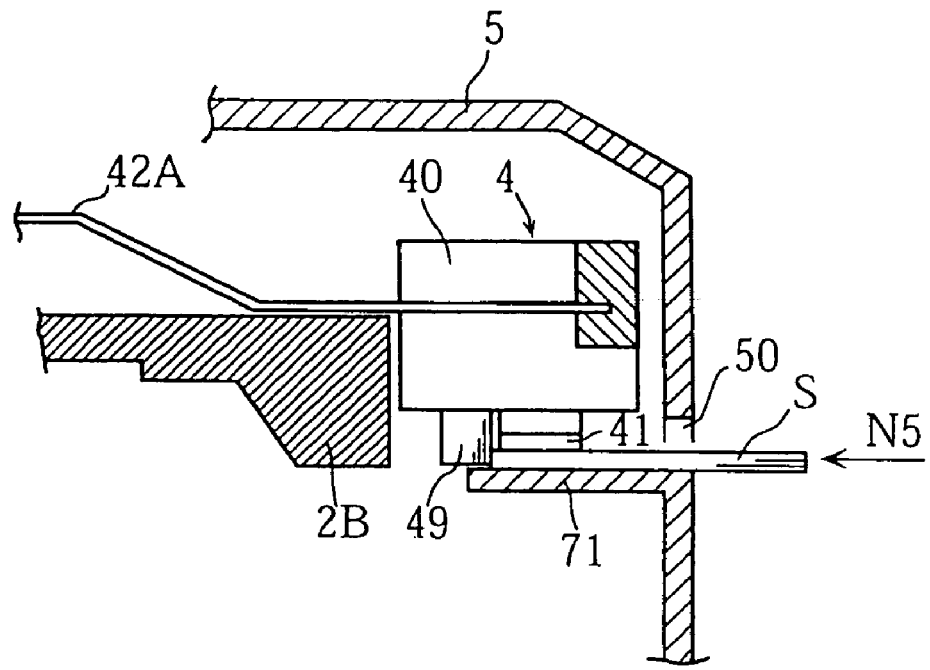
FIG. 11 is a sectional view of a primary portion, showing another embodiment of the present invention.
Figure 12:
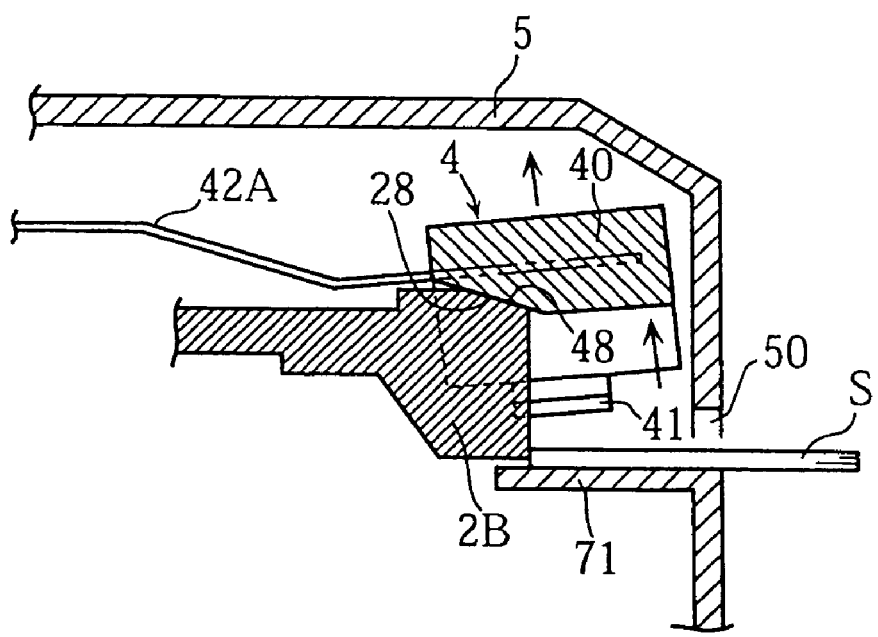
FIG. 12 is a sectional view of a primary portion, showing still another embodiment of the present invention.

FIG. 11 and FIG. 12 show another embodiment of the present invention. In these drawings, components identical with or similar to those used in the above embodiments are indicated by the same alphanumeric codes.

In a constitution shown in FIG. 11, a block 40 of a connector 4 has a lower surface provided with a projection serving as a stopper 49. The stopper 49 is on an opposite side of an opening 50 of the casing 5, sandwiching the terminals 41 of the connector 4 in between, and extending lower than the terminals 41.

An advantage according to such a constitution is that during the measurement of blood glucose level with the sensor S sandwiched by the terminals 41 of the connector 4 and the support 71, the stopper 49 prevents the sensor S from being pushed back in case the user happens to push the tip of sensor S in a direction indicated by Arrow N5. Thus, it becomes possible to prevent the sensor S from accidentally being pushed into the casing 5, which increases convenience.

In a constitution shown in FIG. 12, a second movable member 2B has an upper surface formed with a forward down-sloping (rightward down-sloping in the drawing) ramp 48. A connector 4 has a ramp 28 which makes contact with the ramp 48. These ramps 48, 28 make contact with each other when the second movable member 2B makes a forward movement closer to an opening 50. The connector 4 is raised by the contacting operation.

According to such a constitution, it becomes possible to raise the connector 4 when the second movable member 2B makes a forward movement to discharge a sensor S on a support 71. This makes possible to push the sensor S out of the casing 5 without allowing the sensor S to rub against the electrodes 41 of the connector 4, resulting in enhanced protection of the electrodes 41 from wear. It should be appreciated that the ramps for raising the connector may not necessarily be made on both of the connector 4 and the second movable member 2B, but only on either one of the two.

The present invention is not limited to what has been described in the embodiment above. Specific construction of each part and component of the measuring instrument according to the present invention may be varied in many ways.

A pressurizing means according to the present invention may be realized by a reciprocating component such as a reciprocating cylinder. The cylinder directly supports the connector, and moves the connector to and from the sensor. Alternatively to pressing the connector to the sensor, the sensor may be pressed against the connector in order to achieve the press fit between the connector and the sensor.

The measuring instrument according to the present invention is not limited to those for measuring blood glucose levels, and can be made as measuring instruments for various kinds of targets in the medical field or other technical fields other than medication. Therefore, there is no limitation to the kinds or specific construction of the measuring article.

The present invention places no limitation to a structure to which the measuring article is set. For example, a package of a plurality of measuring articles may be loaded in an appropriate location of the measuring instrument, so that the measuring instrument is dispensed from this package to a predetermined measuring position. The number of measuring articles loaded in the measuring instrument may not be plural, and the structure may only allow a single measuring article to be set at one time. The connector may not include a resin block, but may be provided only by electrodes for example, which make contact with the measuring article. The measuring article transporting means according to the present invention can be provided by many different structures. Further, mechanical operations in the measuring instrument may not be manually operated. Alternatively for example, an electric motor may be used to drive necessary components.

The invention claimed is:

1. A measuring instrument comprising:
   measuring article transporting means for transportation of a measuring article from a predetermined set position to a measuring position for contact with a connector; and
   a measurement circuit for performing a measuring operation using the measuring article upon connection of the measuring article with the connector,
   wherein the measuring instrument further comprises pressurizing means for moving at least one of the measuring article and the connector toward and into pressing contact with the other when the measuring article is at the measuring position,
   wherein the pressurizing means includes a mechanism for moving the connector to the measuring article in a reciprocating manner,
   wherein the connector moves away from the measuring position for avoiding contact with the measuring article during the transportation of the measuring article to the measuring position,
   wherein the pressurizing means includes a supporting member supporting the connector and a pressing member separate from the supporting member,
   the pressing member making a first operation of pressing a first surface of the supporting member to deform the supporting member for a movement of the connector away from the measuring article, and a second operation of pressing a second surface of the supporting member which is a surface away from the first surface to deform the supporting member for a movement of the connector toward the measuring article.

2. The measuring instrument according to claim 1, wherein the supporting member extends in a predetermined direction and includes a first and a second cutout recesses spaced from each other longitudinally of the supporting member, the pressing member making a forward movement from a predetermined initial position on a side of the first surface of the supporting member, passing through the first cutout recess after the first operation and moving on a side of the second surface of the supporting member, then making a rearward movement in a reverse direction of the forward movement after the second operation, passing through the second cutout recess end coming back to the initial position.

3. The measuring instrument according to claim 2, wherein the supporting member includes a ramp between the first and the second cutout recesses, the pressing member pressing the ramp during the forward movement and the rearward movement to make the first and the second operations.

4. The measuring instrument according to claim 3, wherein the measuring article transporting means includes a movable member reciprocatable longitudinally of the supporting member, the pressing member being supported by the movable member for reciprocation with the movable member.

5. The measuring instrument according to claim 1, further comprising a stopper contactable with a rear end of the measuring article for preventing refraction of the measuring article once the measuring article is placed at the measuring position.

6. The measuring instrument according to claim 5, wherein the stopper extends out of the connector, the connector moving away from the measuring position during the transportation of the measuring article to the measuring position for preventing interference between the stopper and the measuring article, the connector moving closer to the measuring article after the transportation of the measuring article for placing the stopper behind the measuring article.

7. The measuring instrument according to claim 1, further comprising a casing formed with an opening for exposure of at least part of the measuring article placed at the measuring position, the measuring article transporting means being capable of discharging the measuring article from the opening out of the casing.

8. The measuring instrument according to claim 7, wherein the connector moves away from the measuring position when the measuring article is discharged from the opening out of the casing.

9. The measuring instrument according to claim 8, wherein the measuring article transporting means includes a movable member for pushing to move the measuring article, the movable member moving to discharge the measuring article out of the casing while making contact with the connector thereby pushing the connector away from the measuring position.

10. A measuring instrument comprising:

measuring article transporting means for transportation of a measuring article from a predetermined set position to a measuring position for contact with a connector; and a measurement circuit for performing a measuring operation using the measuring article upon connection of the measuring article with the connector, wherein the measuring instrument further comprises pressurizing means for moving at least one of the measuring article and the connector toward and into pressing contact with the other when the measuring article is at the measuring position, wherein the measuring instrument further comprises a stopper contactable with a rear end of the measuring article for preventing retraction of the measuring article once the measuring article is placed at the measuring position, wherein the stopper extends out of the connector, the connector moving away from the measuring position during the transportation of the measuring article to the measuring position for preventing interference between the stopper and the measuring article, the connector moving closer to the measuring article after the transportation of the measuring article for placing the stopper behind the measuring article.

* * * * *